United States Patent [19]

Thompson et al.

[11] Patent Number: 5,118,524
[45] Date of Patent: Jun. 2, 1992

[54] VASCULAR BIOMATERIAL

[75] Inventors: Michael Thompson, Mississauga; Neil B. McKeown; Peter G. Kalman, both of Toronto, all of Canada

[73] Assignee: The Toronto Hospital, Toronto, Canada

[21] Appl. No.: 582,616

[22] Filed: Sep. 14, 1990

[51] Int. Cl.⁵ ............................................. A61F 2/00
[52] U.S. Cl. ...................................... 427/2; 623/1; 623/12; 427/235; 427/250; 427/273
[58] Field of Search ............... 427/2, 40, 235, 296, 427/336, 404, 271, 273, 250; 623/1, 12

[56] References Cited

U.S. PATENT DOCUMENTS

| | | | |
|---|---|---|---|
| 4,167,045 | 9/1979 | Sawyer | 427/2 |
| 4,537,791 | 8/1985 | Tarjan | 427/2 |
| 4,678,468 | 7/1987 | Hiroyoshi | 623/1 |
| 4,846,834 | 7/1989 | von Recum et al. | 427/2 |
| 4,859,538 | 8/1989 | Ribi | 427/2 |
| 4,891,407 | 1/1990 | Mitchell | 525/104 |
| 4,937,369 | 6/1990 | Chapman et al. | 525/379 |
| 4,946,903 | 8/1990 | Gardella et al. | 428/409 |
| 4,973,493 | 11/1990 | Guire | 427/2 |
| 5,080,924 | 1/1992 | Kamel et al. | 427/40 |

OTHER PUBLICATIONS

Kallury et al., J. Org. Chem. 52:5478 (1987).
Kallury et al., Analytica Chimica Acta, 225: 369 (1989).
Formichi et al., Annals of Vascular Surgery, 2:14 (1988).

Primary Examiner—Michael Lusignan
Assistant Examiner—Diana L. Dudash
Attorney, Agent, or Firm—Timothy R. Kroboth

[57] ABSTRACT

The present invention provides a vascular biomaterial that includes expanded PTFE and a haemocompatible membrane covalently bonded thereto. Also provided is a process for making the vascular biomaterial that involves chemically modifying the surface of expanded PTFE to provide a surface partially covered with for instance, a hydroxyl moiety, and covalently bonding a haemocompatible membrane to the chemically modified surface of expanded PTFE.

17 Claims, No Drawings

VASCULAR BIOMATERIAL

BACKGROUND OF THE INVENTION

This invention relates to a vascular biomaterial, particularly to the use of expanded polytetrafluoroethylene in a vascular biomaterial.

Autologous saphenous vein is the conduit of choice for replacement of small diameter, diseased arteries in cardiac and vascular surgery. However, in certain cases, it is unsuitable for use and expanded polytetrafluoroethylene (PTFE) has served as the best synthetic alternative.

Expanded PTFE has a delicate microfibrillar, porous structure. Typically, the microfibrils have a cross-sectional diameter of less than about 1 micrometer. Long-term applications of an expanded PTFE graft as an arterial substitute, are limited by a high incidence of occlusion by thrombus as a result of incompatibility with blood. Lack of good tissue ingrowth is another problem.

As illustrated by U.S. Pat. No. 3,635,938 to Ryan et al, and by Roberts, Ryan et al, *Journal of Applied Polymer Science*, 20: 255 (1976), it is known to bond PTFE to an adhesive and to increase gold-Teflon FEP joint strength. In the Ryan patent, activated aluminum foil is used to form an intermediate PTFE-aluminum composite, and the aluminum foil is dissolved in a sodium hydroxide solution.

In the Roberts publication, an aluminum layer is deposited onto Teflon FEP by evaporation, the aluminum layer is removed with a sodium hydroxide solution, and a gold-Teflon FEP composite is formed. Electric properties of the virgin polymer material were unaffected, and XPS analysis was concluded to show oxygen-containing hydrocarbon species in the surface region of a chemically-modified Teflon FEP.

Also known is the modification of surface chemistry of PTFE by the introduction of oxygenated moieties, as exemplified by Costello and McCarthy, *Macromolecules*, 20: 2819 (1987), Morra et al, *Langmuir*, 5: 872 (1989), and the work of J. A. Gardella, Jr. and T. G. Vargo at the University at Buffalo, S.U.N.Y., Buffalo, N.Y. The Costello process creates surface-residing hydroxyl groups by a reduction step followed by hydroboration and an oxidation step. However, a drawback is the depth to which the reduction step etches into the bulk of the PTFE, with a depth of about 150 to 20,000 Angstroms being cited. Expanded PTFE is said to react with the reducing agent.

The Morra et al procedure utilizes oxygen plasma to treat PTFE. The University at Buffalo work utilizes RFGD plasmas comprising water or methanol vapors mixed with hydrogen gas to hydroxylate expanded PTFE, and describes the preparation of silanized expanded PTFE by treatment with (3-aminopropyl)triethoxysilane, and subsequent derivation with FITC; however, such work changes underlying microfibrils and has not controllably provided for significantly varied degrees of hydroxlation.

The design of polymers which mimic the haemocompatible surface of the endothelial cell wall, is exemplified by Hayward and Chapman, *Biomaterials*, 5: 135 (1984). This prior art describes a haemocompatible membrane formed of phospholipid polymers.

As illustrated by Albrecht et al, *Biochimica et Biophysica Acta*. 687: 165 (1982), phospholipid membranes have been immobilized onto PTFE surfaces using Langmuir-Blodgett monolayer deposition followed by cross-linking polymerization of the membrane. Other work lacking covalent bonding between a polymer surface and a haemocompatible compound is exemplified by *Chemical Abstracts*, 102(14): 119697x (1984), which plasma treats a polymer surface and heparinizes the resultant surface after an intermediate surfactant exposure step.

Covalent bonding of haemocompatible compounds to various substrates other than PTFE is known, as exemplified by Jozefowicz and Jozefowicz, *Pure & Appl. Chem.*, 56(10): 1335 (1984), *Chemical Abstracts*, 105(6): 49107r (1986), and U.S. Pat. No. 4,824,529 to Thompson et al. The *Chemical Abstracts* publication discloses a silane coupling agent, and Example 5 of the Thompson patent describes the use of (3-aminopropyl)triethoxysilane as a coupling agent. Covalent bonding produces a stabilized biomaterial.

Therefore, there is a need for an expanded PTFE to which a haemocompatible membrane layer has been covalently bonded, for use in a vascular biomaterial. Importantly, the expanded PTFE would continue to possess adequate physical properties to ensure safe clinical use. Additionally, it would be advantageous if good tissue ingrowth were promoted. Likewise, a process for making such a vascular biomaterial is needed.

SUMMARY OF THE INVENTION

It is accordingly an object of the present invention to provide an expanded PTFE to which a haemocompatible membrane layer has been covalently bonded, for use in a vascular biomaterial.

It is a further object of the present invention to maintain adequate physical properties of the expanded PTFE to ensure safe clinical use.

It is a still further object to promote good tissue ingrowth.

It is an even further object to provide a process for making such a vascular biomaterial.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided a vascular biomaterial that includes expanded PTFE. Surface microfibrils of the expanded PTFE have a surface layer modified to a depth of no greater than about 100 Angstroms. A haemocompatible membrane layer is covalently bonded to the modified surface layer of the expanded PTFE.

By the term "surface microfibrils" is meant those microfibrils which are exposed to the biological milieu. In a preferred embodiment, the haemocompatible membrane layer is on one surface of the expanded PTFE, and the other surface of the expanded PTFE is provided with hydrophilic character.

Also provided is a process for making the vascular biomaterial. By the process, the haemocompatible membrane layer is covalently bonded to the modified surface layer of the expanded PTFE via a chemically reactive moiety suitable for covalent bonding. Prior to the bonding, the modified surface layer has a density of the chemically reactive moiety sufficient to immobilize a haemocompatible membrane onto the expanded PTFE.

Also provided is a process for preparing a vascular graft. By the process, surface microfibrils of the outer surface of tubular, expanded PTFE are provided with a layer of a surface modification-promoting metal thereon. Thereafter, the metal-coated, tubular expanded PTFE is inverted to provide the metal layer on the luminal surface, and the metal layer is removed to provide the surface microfibrils of the luminal surface with a surface layer modified to a depth of no greater than about 100 Angstroms, and partially covered with a chemically reactive moiety suitable for covalent bonding. Density of the chemically reactive moiety is sufficient to immobilize a haemocompatible membrane onto the luminal surface. A haemocompatible layer is then covalently bonded to the luminal surface of the tubular, expanded PTFE. In a preferred embodiment, the tissue surface of the tubular, expanded PTFE is modified to be hydrophilic.

DETAILED DESCRIPTION OF THE INVENTION

As explained above, the present invention is directed to an improved vascular biomaterial that includes an expanded PTFE substrate, and to a process for manufacturing the biomaterial. The vascular biomaterial may be a patch or in tubular form. Advantageously, a vascular biomaterial in accordance with the present invention, is haemocompatible, and the integrity of the delicate fibrils of which expanded PTFE is composed, is maintained. Importantly, adequate physical properties of the expanded PTFE to ensure safe clinical use are preserved. Such properties include water entry pressure, tensile strength, burst strength and suture retention strength, and are described in McClurken et al, *Vascular Graft Update: Safety and Performance*, ASTM STP 898, Philadelphia, 1986, pp. 82-94, which article is incorporated herein by reference.

Haemocompatibility is provided by a suitable membrane layer covalently bonded to the expanded PTFE. An antithrombogenic or non-thrombogenic membrane layer may be used. The membrane layer may be formed of phospholipids, synthetic or naturally occurring, or antithrombogenic compounds such as heparin, urokinase, streptokinase, prostacyclin and prostacyclin derivatives.

In vascular biomaterial in accordance with the present invention, the surface microfibrils of the expanded PTFE have a modified surface layer, beneficially, the remaining microfibrils are virgin or have an unmodified surface layer. The haemocompatible membrane layer is covalently bonded to the modified surface layer. Prior to covalent bonding, the modified surface layer is partially covered by chemically reactive moieties such as hydroxyl, amino and carboxylic acid moieties, suitable for covalent bonding to be effected.

Modification of the surface layer of the surface microfibrils should be to a depth of no greater than about 100 Angstroms. Advantageously, the depth of surface layer modification is no greater than about 50 Angstroms, with a depth of about 25 to 35 Angstroms being beneficial. From the foregoing description, it will be understood that a surface selective process is needed to provide an expanded PTFE suitable for usage as a substrate for a vascular biomaterial, in particular for modifying the surface layer of surface microfibrils to a limited depth, and for maintaining the delicate microfibrillar structure.

Prior to covalent bonding, the surface microfibrils will be partially covered by the chemically reactive moiety at a density of at least about 2%. Such a density is sufficient to provide for covalent bonding of a haemocompatible membrane layer to expanded PTFE. A typical density provided by a preferred embodiment of a surface selective process in accordance with the present invention, is at least about 4 to 7%, with a density of at least about 8 to 13% being preferred, and a density of at least about 14 to 22% being highly preferred. The ability to control the density of the coverage of the chemically reactive moiety is an important feature of a surface selective process in accordance with the present invention.

Covalent bonding of the membrane layer to expanded PTFE may be by direct attachment via the chemically reactive moieties, or by attachment to a suitable cross-linking agent covalently bonded via the chemically reactive moieties. Suitable cross-linking agents include reactive silanes such as amino moiety-containing, alkoxy- or clorosilanes. A particularly suitable reactive silane is an aminoalkyl-silane having one or more displaceable alkoxy moieties such as (3-aminopropyl)-triethoxysilane (APTES). A cross-linking agent of this type will not only covalently bond to expanded PTFE through the chemically reactive moieties but also will cross-link, and is very suitable when the modified surface layer has a density of the chemically reactive moiety of less than about 4%.

An important feature of a surface selective process in accordance with the present invention, is that the process can be used to provide a modified surface on both sides of a vascular graft, or solely on one side of a vascular graft, for instance one side of a tubular, vascular graft. Different properties are required for the luminal and tissue surfaces of a tubular, vascular graft: the luminal surface should be haemocompatible, and the tissue surface should promote good tissue ingrowth. It is therefore advantageous to be able to differentiate the chemistry of both sides.

In regard to the foregoing advantage, a surface selective process in accordance with the present invention, can be used to increase the hydrophilic character of the tissue surface of expanded PTFE. For instance, the surface microfibrils of the tissue surface could be hydroxylated. A hydroxyl group density of at least about 2%, typically at least about 4-7%, and if desired, from about 8-22%, can be effected. Thereafter, if desired, the hydroxyl moieties could be subjected to further chemical reaction such as esterification, to modify the hydrophilic character. We have found that cell adhesion and protein absorption are promoted by, for instance, about 16 to 18% hydroxyl group density. Thus, a surface selective process in accordance with the present invention, is able to provide both a chemically reactive moiety suitable for covalent bonding to be effected, ad hydrophilic character.

Prior to the first step of the surface selective process of the present invention, expanded PTFE is cleaned with tetrahydrofuran to remove surface impurities. A Soxhelet extractor is conveniently used.

In accordance with the process of the present invention, the surface microfibrils of expanded PTFE are thereafter provided with a thin layer of a surface modification-promoting metal. Although any such reactive metal including the alkali metals, suitable for promoting the formation of chemically reactive moieties, may be used, aluminum is particularly suitable. An aluminum layer, when removed as later described in accordance with the process of the present invention, produces a modified surface layer having hydroxyl moieties as the chemically reactive moiety, and also useful for increasing the hydrophilic character of the tissue surface of expanded PTFE.

Vacuum vapour deposition or metal sputtering may be used to form the metal layer. When vacuum deposition is employed, conventional vacuum metal deposition equipment may be used. During the deposition, a pressure of not greater than about $5 \times 10^{-6}$ torr is beneficially used, and the rate of deposition is suitably maintained below about 2 Angstroms per second. Typically, the thickness of the metal layer will range from about 200 to 1000 Angstroms, with a thickness of about 300 to 400 Angstroms being convenient. The deposition process is surface selective: the surface layer of surface microfibrils is metal-coated; beneficially, the remaining microfibrils are uncoated.

In accordance with the process of the present invention, when an aqueous, metal layer-removing composition is to be used, the metal-coated, expanded PTFE is advantageously pre-wetted so as to enhance the activity of the metal layer-removing composition, and in particular so as to provide for removal of the metal layer from interstitial spaces of the surface microfibrils. When the metal layer is an aluminum layer, the metal layer-removing composition is an aqueous base such as sodium hydroxide. In such case, the pre-wetting liquid may be a water-miscible organic solvent such as ethanol, or an aqueous solution of a suitable surfactant.

Suitably, the metal-coated, expanded PTFE is pre-wetted by immersion into the pre-wetting liquid for a period of time ranging from about 30 seconds to about 2 minutes. The pre-wetting liquid is thereafter replaced with water by for instance, washing the expanded PTFE with ultra-pure water under ultrasonic agitation.

Then, in accordance with the process of the present invention, the metal layer is removed from the expanded PTFE by use of a metal layer-removing composition such as in the case of an aluminum layer, an aqueous solution of sodium hydroxide. Layer removal is conveniently accomplished by immersion of the metal-coated, expanded PTFE into, in the case of an aluminum layer, an ultrasonically agitated, aqueous solution of sodium hydroxide (suitably about 0.1 molar concentration) until no aluminum can be observed, and then allowing the mixture to stand for about 10 minutes. Afterwards, the expanded PTFE is thoroughly washed by for instance, ultrasonic agitation with copious quantities of ultra-pure water.

When aluminum is the active metal and the foregoing deposition and layer removal steps are employed, modification of the surface layer of the surface microfibrils will typically be to a depth of no greater than about 25 to 35 Angstroms. When one cycle of deposition and layer removal is carried out, a hydroxyl moiety density of about 4-7% is obtained; whereas two cycles of deposition and layer removal increase hydroxyl density to about 8 to 13%. When repeated a third time, the hydroxyl density is increased to about 14 to 22%; however, when repeated a fourth time, the hydroxyl density will decrease. Thus, it can be understood that by the use of vacuum deposition, modification of expanded PTFE can be limited to the surface microfibrils, the depth of the surface layer modification is limited, and the density of the chemically reactive moiety can be controlled.

In accordance with the process of the present invention, expanded PTFE partially covered with chemically reactive moieties suitable for covalent bonding to be effected, is used to covalently immobilize suitable haemocompatible, membrane layer-forming compounds either by direct attachment via the chemically reactive moieties, or by indirect attachment through a suitable cross-linking agent such as (3-aminopropyl)triethoxysilane (APTES). In either case, covalent bonding is conveniently carried out with a stoichiometric excess of the compound to be covalently bonded to the expanded PTFE.

The covalent bonding reaction should be effected in a suitable solvent that is non-reactive with the reaction starting materials. A suitable organic solvent for a hydroxylated, expanded PTFE is freshly distilled, dry toluene. The covalent bonding reaction is conveniently run at ambient temperature, with stirring, in an inert atmosphere. Sufficient time is permitted for the reaction to be completed.

When preparing a tubular, vascular graft in accordance with the process of the present invention, the exterior surface of the tubular expanded PTFE is conveniently provided with the metal layer. Prior to removal of the metal layer in preparation for the covalent bonding step, the tubular, metal-coated, expanded PTFE is advantageously inverted so that the chemically reactive moieties will be on the luminal surface. Therefore, for example, if in the case of an aluminum layer, it is desired to have a hydroxyl density of about 14 to 22%, then the inversion step is carried out after two cycles of deposition and removal, and after the third deposition step. By this procedure, the metal layer beneficially protects the underlying modified surface layer during the inversion process.

After covalently immobilizing the membrane on one surface of the expanded PTFE, the foregoing deposition and removal steps may be repeated on the opposite surface to increase the hydrophilic character thereof.

The modified, expanded PTFE prepared by the surface selective process of the present invention, has insignificant change in the surface morphology. Therefore, it will be understood that the surface selective process of the present invention, provides surface microfibrils with a chemically modified surface layer, with insignificant change in the surface morphology.

In the Examples that follow and throughout this description and the claims set forth below, all procedures are carried out at ambient temperature and pressure, unless otherwise specified. X-Ray Photoelectron Spectroscopy (XPS) is at a 90° electron detection angle relative to the polymer surface.

EXAMPLE 1

A 40 mm long section of tubular, expanded PTFE (ePTFE) having a diameter of 6 mm, available from Goretex, is cleaned for a period of 4 hours using a Soxhelet extractor with THF as the cleansing solvent. Thereafter, the tubular section is cut lengthwise and attached as a flat piece of ePTFE (40 mm × 19 mm × 0.5 mm) to a glass microscope slide by means of double sided adhesive tape. The results of an XPS elemental analysis of the unmodified, exposed ePTFE surface are set forth below, and indicate the lack of oxygen-containing species.

A 400 Angstrom thick film of aluminum metal is then deposited onto the surface microfibrils of the exposed ePTFE surface using conventional vacuum metal deposition equipment. During deposition, a pressure of not greater than $5 \times 10^{-6}$ torr is used, and the rate of deposition is maintained below 2 Angstroms per second.

The resultant metal-coated ePTFE is pre-wetted, in preparation for the metal layer-removal step, by immersion into ethanol (100ml) for 1 minute, and is thereafter washed with ultra-pure water ($2 \times 100$ml) for 10 minutes under ultrasonic agitation to replace the ethanol with water. Then, the aluminum layer is removed from the ePTFE surface by immersion of the metal-coated ePTFE into an ultrasonically agitated, aqueous solution of sodium hydroxide (0.1 molar concentration) for 15 minutes. Afterwards, ultrasonic agitation for 20 minutes with ultrapure water ($3 \times 100$ml) is used for thorough washing of the ePTFE.

An XPS elemental analysis of the re-exposed ePTFE surface is set forth below, and reveals that the modified surface layer has a hydroxyl group density of about 4%.

The foregoing deposition, pre-wetting and layer removal techniques are repeated on the modified, ePTFE. An XPS analysis of the further modified, re-exposed ePTFE surface is set forth below, and reveals that the modified surface layer has a hydroxyl group density of about 10%.

The foregoing deposition, pre-wetting and layer removal techniques are repeated on the modified, ePTFE ($2 \times$ Al). An XPS analysis of the resultant modified, re-exposed ePTFE surface is set forth below, and shows a further increase in the percentage C, a further decrease in the percentage F, and a further increase in the percentage O. The modified surface layer has a hydroxyl group density of about 16%.

|  | % C | % F | % O |
| --- | --- | --- | --- |
| Unmodified ePTFE | 33 | 67 | 0 |
| Modified ePTFE 1 × Al | 38 | 60 | 2 |
| Modified ePTFE 2 × Al | 43 | 52 | 5 |
| Modified ePTFE 3 × Al | 49 | 44 | 7 |

Thereafter, under anhydrous conditions, the modified, ePTFE ($3 \times$ Al) is refluxed with a selected chlorosilylated phospholipid (0.1 g, 0.15 mmol), for instance 3-hexanoyl-2-[9-((chlorodimethylsilyl)oxy-nonanoyl]-sn-glycerophosphatidylcholine (see Kallury et al, *J. Org. Chem.*, 52: 5478 (1978)), in dry chloroform (25 ml) and dry pyridine (0.2 ml) in a nitrogen atmosphere for 24 hours. The solution is decanted off, and the ePTFE is washed several times with chloroform and methanol. As a result, there is produced a vascular biomaterial in accordance with the present invention.

EXAMPLE 2

A 50 cm long section of tubular ePTFE having a diameter of 4 mm is cleaned for a period of 4 hours using a Soxhelet extractor with THF as the cleansing solvent. Thereafter, a 400 Angstrom thick film of aluminum metal is deposited on the surface microfibrils of the outer surface of the tubular ePTFE using conventional vacuum metal deposition equipment. During deposition, a pressure of not greater than $5 \times 10^{-6}$ torr is used, and the rate of deposition is maintained below 2 Angstroms per second.

The resultant section of tubular ePTFE is thereafter pre-wet and treated in accordance with the procedure of Example 1 to remove the aluminum layer. The surface modified, tubular ePTFE is then subjected again to the foregoing techniques of the deposition, pre-wetting, layer removal and deposition steps.

Then the resultant section of tubular ePTFE is inverted to provide the aluminum layer on the luminal surface, and thereafter again subjected to pre-wetting and layer removal steps in accordance with the procedure of Example 1, to remove the aluminum layer from the luminal surface. As a result, the surface microfibrils of the luminal surface have a modified surface layer with a hydroxyl group density of about 18%.

Thereafter, the modified, tubular ePTFE ($3 \times$ Al) is immersed in 50 ml of dry toluene. 0.5 ml of freshly distilled (3-aminopropyl)triethoxysilane (APTES) is added to the toluene with stirring, to produce a 1% solution by volume of APTES, and the mixture is maintained under a nitrogen blanket for 24 hours at room temperature, with continuous stirring. Afterwards, a Soxhelet extractor with THF as the cleansing solvent is used to remove excess APTES. As a result, the luminal surface of the tubular ePTFE is silanized.

The silanized, tubular ePTFE is immersed in 25 ml of chloroform and treated with monomethyl ester of azelaic acid (1 mmol), DCC (1 mmol) and DMAP (0.1 mmol). The mixture is then stirred for 24 hours at room temperature under nitrogen, and the supernatant liquid is decanted off. The tubular ePTFE is washed several times with THF and then treated with aqueous 1% sodium hydroxide (10 ml) for 24 hours to hydrolyze the methyl ester. The hydrolyzed surface is washed several times, and the resulting tubular ePTFE is treated in dry chloroform (25 ml) with lyso-caprylyllecithin (0.1 g), DCC (50 mg) and DMAP (20 mg). The mixture is stirred under nitrogen for 72 hours. The supernatant liquid is decanted off and the tubular ePTFE is washed several times with chloroform-methanol (1+1). As a result, there is produced a vascular biomaterial in accordance with the present invention.

Thereafter, the tissue surface of the resultant vascular biomaterial is subjected to the foregoing techniques of the deposition, pre-wetting and layer removal steps. As a result, the surface microfibrils of the tissue surface have a modified surface layer with a hydroxyl group density of about 5%.

The above examples are illustrative of the present invention, and are not in any way to be interpreted as limiting the scope of the invention. It will be apparent that modifications and variations are possible without departing from the scope of the invention defined in the appended claims. Several changes or modifications have been briefly mentioned for purposes of illustration.

We claim:

1. A process for preparing a vascular biomaterial, said process comprising providing an expanded polytetrafluoroethylene (PTFE) in which surface microfibrils of a first surface of said expanded PTFE have a surface layer modified to a depth of no greater than about 100 Angstroms, and in which the modified surface layer has a density of a chemically reactive moiety suitable for covalent bonding, sufficient to immobilize a haemocompatible membrane onto said expanded PTFE; and covalently bonding a haemocompatible membrane layer to said first surface of said expanded PTFE via the chemically reactive moieties of said first surface of said expanded PTFE; wherein said surface microfibrils having said modified surface layer are provided by the steps of providing surface microfibrils of a first surface of said expanded PTFE with a layer of a surface modifications-promoting metal thereon, and of thereafter removing said metal layer.

2. The process of claim 1, further comprising subsequent to the step of providing said expanded PTFE but prior to said covalent bonding step, covalently bonding a linking agent which is capable of covalently bonding with said chemically reactive moiety and thereafter with said haemocompatible membrane layer, directly to said chemically reactive moiety.

3. The process of claim 1, wherein said chemically reactive moiety is a hydroxyl moiety.

4. The process of claim 1, further comprising the step of providing a second surface of said expanded PTFE with a hydrophilic character.

5. A process for preparing a tubular, vascular graft, said process comprising providing surface microfibrils of the outer surface of tubular, expanded PTFE with a layer of a surface modification-promoting metal thereon, inverting the metal-coated, tubular expanded PTFE to provide the metal layer on the luminal surface, removing said metal layer to provide the surface microfibrils of said luminal surface with a surface layer modified to a depth of no greater than about 100 Angstroms, and partially covered with a chemically reactive moiety suitable for covalent bonding, the density o the chemically reactive moiety being sufficient to immobilize a haemocompatible membrane onto said luminal surface; and covalently bonding a haemocompatible membrane layer to said luminal surface of the tubular expanded PTFE via the chemically reactive moieties of said luminal surface.

6. The process of claim 5, further comprising subsequent to the step of providing said expanded PTFE but prior to said covalent bonding step, covalently bonding a linking agent which is capable of covalently bonding with said chemically reactive moiety and thereafter with said haemocompatible membrane layer, directly to said chemically reactive moiety.

7. The process of claim 5, further comprising subsequent to said covalent bonding step, the step of providing a second surface of said expanded PTFE with a hydrophilic character, said second surface being the tissue-contacting surface.

8. The process of claim 5, wherein said layer of a surface modification-promoting metal is provided by vacuum deposition whereby microfibrils other than said surface microfibrils are uncoated by said metal and thereby remain virgin after said metal layer removal.

9. The process of claim 5, wherein said surface modification-promoting metal is a hydroxylation-promoting metal.

10. The process of claim 5, further comprising prior to the metal layer removal step, treating the metal-coated, expanded PTFE so as to provided for removal of the metal layer from interstitial spaces of the surface microfibrils.

11. The process of claim 5, wherein said surface layer is modified to a depth no greater than about 25 to 35 Angstroms.

12. The process of claim 5, wherein said density of said chemically reactive moiety is from about 14 to 22%.

13. The process of claim 1, wherein said layer of said surface modification-promoting metal is provided by vacuum deposition, whereby microfibrils other than said surface microfibrils are uncoated by said metal and thereby remain virgin after said metal layer removal.

14. The process of claim 1, wherein said haemocompatible membrane layer is formed phospholipids.

15. The process of claim 5, wherein said haemocompatible membrane layer is formed of phospholipids.

16. The process of claim 7, wherein surface microfibrils of said tissue-contacting surface are provided with a layer of a surface modification-promoting metal thereon, said metal being a hydroxylation-promoting metal, and wherein said metal layer is thereafter removed to provide the surface microfibrils of said tissue-contacting surface with a surface layer modified to a depth of no greater than about 100 Angstroms, and partially covered with hydroxyl moieties.

17. A process for preparing a vascular biomaterial, said process comprising providing an expanded polytetrafluoroethylene (PTFE) in which surface microfibrils of a first surface of said expanded PTFE have a surface layer modified to a depth of no greater than about 100 Angstroms, and in which the modified surface layer has a density of a chemically reactive moiety suitable for covalent bonding, sufficient to immobilize a haemocompatible membrane onto said expanded PTFE; covalently bonding a haemocompatible membrane layer to said first surface of said expanded PTFE via the chemically reactive moieties of said first surface of said expanded PTFE; and providing a second surface of said expanded PTFE with a hydrophilic character, wherein surface microfibrils of said second surface are provided with a layer of a surface modification-promoting metal thereon, said metal being a hydroxylation-promoting metal, and wherein said metal layer is thereafter removed to provide the surface microfibrils of said second surface with a surface layer modified to a depth of no greater than about 100 Angstroms, and partially covered with hydroxyl moieties.

* * * * *